US006660699B2

(12) United States Patent
Finucane et al.

(10) Patent No.: US 6,660,699 B2
(45) Date of Patent: Dec. 9, 2003

(54) TOILET BAR HAVING A LATENT ACIDIFIER

(75) Inventors: Kevin Michael Finucane, Southbury, CT (US); Bruce Casbarro, Hamden, CT (US); Sudhakar Puvvada, Shelton, CT (US); Joseph J. Podgorsky, Slate Hill, NY (US)

(73) Assignee: Unilever Home & Personal Care USA, Greenwich, CT (US)

( * ) Notice: Subject to any disclaimer, the term of this patent is extended or adjusted under 35 U.S.C. 154(b) by 171 days.

(21) Appl. No.: 09/967,280

(22) Filed: Sep. 28, 2001

(65) Prior Publication Data

US 2003/0134762 A1 Jul. 17, 2003

(51) Int. Cl.$^7$ .................................................. A61K 7/50

(52) U.S. Cl. ....................... 510/141; 510/152; 510/153; 510/155; 510/156; 510/426; 510/428

(58) Field of Search ................................ 510/141, 152, 510/153, 155, 156, 426, 428

(56) References Cited

U.S. PATENT DOCUMENTS

| | | | | |
|---|---|---|---|---|
| 3,030,310 | A | | 4/1962 | Turck, Jr. |
| 3,178,370 | A | | 4/1965 | Okenfuss |
| 3,951,842 | A | | 4/1976 | Prince et al. |
| 4,673,525 | A | | 6/1987 | Small et al. |
| 4,705,644 | A | | 11/1987 | Barone et al. |
| 4,806,273 | A | | 2/1989 | Barone et al. |
| 5,053,159 | A | | 10/1991 | Joshi et al. |
| 5,691,287 | A | | 11/1997 | Villars et al. |
| 5,914,133 | A | | 6/1999 | Tsujino |
| 6,172,026 | B1 | * | 1/2001 | Ospinal et al. ............. 510/355 |
| 6,559,110 | B1 | | 5/2003 | Lopes |

FOREIGN PATENT DOCUMENTS

| | | |
|---|---|---|
| GB | 885332 | 12/1961 |
| GB | 989007 | 4/1965 |
| GB | 1004596 | 9/1965 |
| GB | 1477897 | 6/1977 |
| GB | 2253404 | 9/1992 |
| WO | 98/06810 | 2/1998 |
| WO | 98/38269 | 9/1998 |
| WO | 98/53040 | 11/1998 |

OTHER PUBLICATIONS

International Search Report No. PCT/EP 02/10275, dated Dec. 27, 2002, 4 pp.

* cited by examiner

*Primary Examiner*—Necholus Ogden
(74) *Attorney, Agent, or Firm*—Alan A. Bornstein

(57) ABSTRACT

Mild toilet bar compositions are described that contain harsh to the skin cleansing components, such as soap, and a latent acidifier. The latent acidifier reduces the pH of the toilet bar when used for cleansing but does not substantially affect the hardness of the toilet bar.

56 Claims, No Drawings

TOILET BAR HAVING A LATENT ACIDIFIER

BACKGROUND OF THE INVENTION

1. Field of the Invention

The present invention relates to a toilet bar suitable for topical application for cleansing the human body, such as the skin and hair. In particular, it relates to a toilet bar composition that is mild to the skin and which contains at least one latent acidifier.

2. The Related Art

The following all disclose laundry detergent bar compositions that contain various filler materials. U.S. Pat. No. 4,806,273 issued to Barone, et al. on Feb. 21, 1989 and U.S. Pat. No. 5,053,159 issued to Joshi on Oct. 1, 1991 disclose the use of various water insoluble fillers such as talc, calcium silicate, magnesium silicate, calcium sulfate, silica, bentonite, calcium phosphate and calcium carbonate in synthetic detergent laundry bars. U.S. Pat. No. 3,178,370 issued to Okenfuss on Apr. 13, 1965 discloses detergent laundry bar composition containing a broad range of salts. U.S. Pat. No. 4,705,644 issued to Barone, et al. on Nov. 10, 1987 also teach synthetic detergent laundry bars that contain various insoluble particulate materials and teach that calcium carbonate and talc are especially useful materials therein.

PCT publication no. WO98/06810 to Hauwermeiren, et al., published on Feb. 19, 1998 teaches laundry detergent compositions having filler salts selected from alkali and alkaline-earth metal sulfates & chlorides, with sodium sulfate as a preferred filler. PCT publication no. WO 98/38269 to Ramanan, et al., published on Sep. 3, 1998 discloses a laundry detergent bar with improved physical properties arising from the formation of a complex of calcium and the siliceous material in-situ. PCT publication no. WO 98/53040 to Ramanan, et al., published Nov. 26, 1998 discloses a laundry bar with improved sudsing and physical properties having a metal-anionic sulfonate surfactant complex.

The above patents and publications however, fail to disclose or suggest a mild to the skin toilet bar containing an effective amount of one or more specific latent acidifiers sufficient to provide pH reduction to the bar in the form of an aqueous slurry delta pH of about 0.5 or more, nor a $R_{ys}$ value (as defined below) in the range of about 0.70 to about 1.3. Aqueous slurry delta pH is herein defined as the value obtained when the pH of a 10% aqueous slurry of a bar with the latent acidifier is subtracted from the pH of an aqueous slurry of a bar without the latent acidifier. $R_{ys}$ is herein defined as the ratio of the yield stress of the bar containing the latent acidifier to the yield stress of the bar without the latent acidifier or, $$R_{ys} = \frac{\text{Yield stress of bar with latent acidifier}}{\text{Yield stress of bar without latent acidifier}}$$

Latent acidifiers are limited to organic or inorganic materials that when incorporated into a toilet bar do not substantially convert soaps or other alkaline materials contained in the bar to the free acid form and thus do not degrade the bar's hardness as evidenced by yield stress measurements. As the bar is used with water, the latent acidifiers surprisingly either neutralize harsh soaps, or other alkaline materials contained in the toilet bar, or reduce the pH of the bar through other acid-base interactions, so as to create a mild cleansing action for the skin without substantially degrading the bar's hardness. Latent acidifiers are further limited to compounds that do not release a gas with a change in pH and therefore do not include e.g. carbonates, bicarbonates, sulfites, and the like.

SUMMARY OF THE INVENTION

In one aspect the present invention is a toilet bar, having:

(a) about 0 to about 30% by wt.; preferably about 0 to about 20% by wt.; and more preferably about 0 to about 15% by wt. of a fatty acid soap;

(b) about 15 to about 60%; preferably about 20 to about 55%; and more preferably about 25 to about 50% by wt. of a non-soap anionic surfactant; and (c) a latent acidifier in an effective amount to yield an aqueous slurry delta pH value of more than about 0.5, and preferably more than about 1.0.

In a preferred embodiment, there is at least about 0.1% by wt. of a fatty acid soap; preferably more than about 0.5% by wt.; and more preferably more than about 1.0% by wt.

In another aspect of the present invention is a toilet bar, having (a) about 30 to about 80% by wt. ; preferably about 40 to about 70% by wt.; more preferably about 50% to about 60% by wt. of a fatty acid soap;

(b) about 5 to about 40% by wt. ; preferably about 7 to about 30%; more preferably about 10 to about 20% by wt. of a non-soap anionic surfactant; and (c) a latent acidifier in an effective amount to yield an aqueous delta pH value of more than about 0.5, preferably more than about 1.0.

In a further aspect of the present invention is a toilet bar, having (a) about 40 to about 85% by wt.; preferably 50 to about 80% by wt.; more preferably about 60 to about 75% by wt. of a fatty acid soap;

(b) about 0 to about 10% by wt.; preferably about 0 to about 7% by wt.; more preferably about 0 to about 5% by wt. of a non-soap anionic surfactant; and (c) a latent acidifier in an effective amount to yield a delta pH value of more than about 0.5, preferably more than about 1.0.

In a preferred embodiment of this aspect of the invention, there is more than about 0.1% by wt. of a non-soap anionic surfactant; preferably more than about 0.5% by wt.; and more preferably more than about 1.0% by wt.

DETAILED DESCRIPTION OF THE INVENTION

In one aspect the present invention is a toilet bar, having:

(a) about 0 to about 30% by wt.; preferably about 0 to about 20% by wt.; and more preferably about 0 to about 15% by wt. of a fatty acid soap;

(b) about 15 to about 60%; preferably about 20 to about 55%; and more preferably about 25 to about 50% by wt. of a non-soap anionic surfactant; and (c) a latent acidifier in an effective amount to yield an aqueous slurry delta pH value of more than about 0.5, preferably more than about 1.0.

In a preferred embodiment, there is at least about 0.1% by wt. of a fatty acid soap; preferably more than about 0.5% by wt.; and more preferably more than about 1.0% by wt.

Preferably, the latent acidifier is in the concentration range of about 0.1 to about 20% by wt., preferably about 1 to about 10% by wt. Advantageously, the fatty acid soaps consist of a blend of C6 to C22 soaps, preferably a blend of C12 to C18 soaps. Preferably the non-soap anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof, and the like.

Latent acidifiers may be organic or inorganic compounds, or blends or complexes thereof as mentioned above. Examples of useful organic compounds include the following: acetates, propionates, glycolates, lactates, aluminum-zirconium chlorohydrate glycine complex, and the like. Preferably the latent acidifier is an inorganic salt. Advantageously it is selected from aluminum sulfate, aluminum chloride, aluminum chlorohydrate, aluminum-zirconium trichlorohydrate, aluminum-zirconium trichlorohydrate glycine complexe, zinc sulfate, ammonium chloride, ammonium phosphate, calcium acetate, calcium chloride, calcium nitrate, calcium phosphate, calcium sulfate, ferric sulfate, magnesium chloride, magnesium sulfate, and the like. Most preferably the latent acidifier is calcium sulfate.

Preferably the inventive bar contains an amount of free water less than about 10% by wt., preferably less than about 7% by wt. and most preferably less than about 3% by wt. Free water is herein defined as that quantity of water present in the bar which is able to solvate acidic compounds. This ability is in contrast to bound water, such as the water of crystallization of unsolvated materials, whereby the bound water is unable to solvate acidic materials to the same extent that free water can.

Preferably, the inventive bar is characterized by an $R_{ys}$ value in the range of about 0.70 to about 1.3, preferably about 0.8 to about 1.2.

In another aspect of the present invention is a toilet bar, having (a) about 30 to about 80% by wt. ; preferably about 40 to about 70% by wt.; more preferably about 50% to about 60% by wt. of a fatty acid soap;

(b) about 5 to about 40% by wt. ; preferably about 7 to about 30%; more preferably about 10 to about 20% by wt. of a non-soap anionic surfactant; and (c) a latent acidifier in an effective amount to yield an aqueous delta pH value of more than about 0.5, preferably more than about 1.0.

Preferably this embodiment of the inventive bar contains an amount of free water less than about 25% by wt., preferably less than about 20% by wt. and most preferably less than about 15% by wt.

In a further aspect of the present invention is a toilet bar, having (a) about 40 to about 85% by wt.; preferably about 50 to about 80% by wt.; more preferably about 60 to about 75% by wt. of a fatty acid soap;

(b) about 0 to about 10% by wt.; preferably about 0 to about 7% by wt.; more preferably about 0 to about 5% by wt. of a non-soap anionic surfactant; and (c) a latent acidifier in an effective amount to yield a delta pH value of more than about 0.5, preferably more than about 1.0.

In a preferred embodiment of this aspect of the invention, there is more than about 0.1% by wt. of a non-soap anionic surfactant; preferably more than about 0.5% by wt.; and more preferably more than about 1.0% by wt.

Preferably this embodiment of the inventive bar contains an amount of free water in the range of about 5 to about 30% by wt., preferably in the range of about 7 to about 25% by wt, and most preferably in the range of about 10 to about 20% by wt.

Surfactants

Surfactants are an essential component of the inventive toilet bar composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants

Soaps

The inventive toilet bar may contain soap, preferably it contains at least 0.1% by wt. of soap. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of tallow, and vegetable oil. More preferably the vegetable oil is selected from the group consisiting of palm oil, coconut oil, palm kernal oil, palm stearin, and hydrogenated rice bran oil, or mixtures thereof, since these are among the more readily available fats. Especially preferred is coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. As mentioned above, the soap may preferably be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Superfatting Agent

Free fatty acid, as a superfatting agent may be added to the composition according to the present invention at a level of 2–10% on total actives. This level of free fatty acids can be obtained by the addition of free fatty acids per se or by the addition of a non-fatty acid superfatting agent which protonates a portion of the fatty acid soaps present to form the free fatty acid. Suitable fatty acid superfatting agents include tallow, coconut, palm and palm-kernel fatty acids. Other fatty acids can be employed although the low melting point fatty acids, particularly the laurics, are preferred for ease of processing. Preferred levels of fatty acid are 3–8%, most preferably around 5% on total actives.

Synthetic Anionic Surfactants

The cleansing composition of the present invention may contain one or more non-soap anionic detergents. The anionic detergent active which may be used may be aliphatic sulfonates, such as a primary alkane (e.g., $C_3$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M:$$

and amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R^1CON(CH_3)CH_2CO_2M,$$

wherein $R^1$ ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

The inventive toilet bar composition preferably contains non-soap anionic surfactants, preferably $C_8$–$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

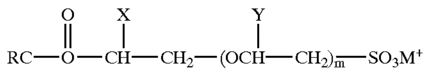

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In another embodiment of the inventive toilet bar, there is less than 5% by wt. of any of the following anionic surfactants: alkyl sulfates, alkyl sulfonates, alkyl benzene sulfonates, alkyl alkoxy sulfates, acyl taurides, acyl sulfates, and polyhydfroxy fatty acid amides either individually or of a blend thereof. Preferably there is less than 1%, and more preferably less than 0.1% by wt. of these surfactants Amphoteric Surfactants One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

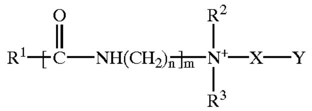

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

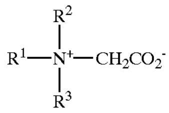

and amido betaines of formula:

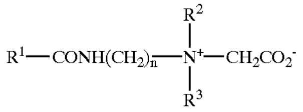

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

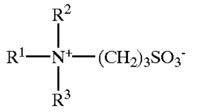

or

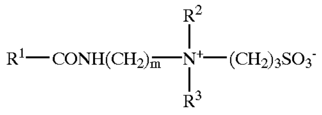

where m is 2 or 3, or variants of these in which $-(CH_2)_3SO_3^-$ is replaced by

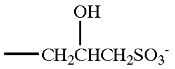

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the toilet bar composition of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR (C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Cationic Surfactants

One or more cationic surfactants may also be used in the inventive self-foaming cleansing composition.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the inventive toilet bar composition of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Humectants such as polyhydric alcohols, e.g. glycerine and propylene glycol, and the like; and polyols such as the polyethylene glycols listed below and the like may be used.

| | |
|---|---|
| Polyox WSR-205 | PEG 14M, |
| Polyox WSR-N-60K | PEG 45M, or |
| Polyox WSR-N-750 | PEG 7M. |

Emollients may be advantageously used in the present invention. The emollient "composition" may be a single benefit agent component or it may be a mixture of two or more compounds one or all of which may have a beneficial aspect. In addition, the benefit agent itself may act as a carrier for other components one may wish to add to the inventive toilet bar.

Hydrophobic emollients, hydrophilic emollients, or a blend thereof may be used. Preferably, hydrophobic emollients are used in excess of hydrophilic emollients in the inventive toilet bar composition. Most preferably one or more hydrophobic emollients are used alone. Hydrophobic emollients are preferably present in a concentration greater than about 5% by weight, more preferably about 10% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters; magnesium, calcium, copper, zinc and other metallic components;

(l) sunscreens such as octyl methoxyl cinnamate (Parsol MCX) and butyl methoxy benzoylmethane (Parsol 1789);

(m) phospholipids;

(n) antiaging compounds such as alpha hydroxy acids, beta hydroxy acids; and (o) mixtures of any of the foregoing components, and the like.

Preferred emollient benefit agents are selected from fatty acids, triglyceride oils, mineral oils, petrolatum, and mixtures thereof. Further preferred emollients are fatty acids.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE 1

Aqueous Slurry pH Testing

Various inventive and comparative compounds were formulated with three separate toilet bar bases, 1, 2, and 3 at the 10% by wt. level and their aqueous slurry pH (see method below) was compared to a control shown in table 1. Inventive latent acidifiers are designated "I" and comparative compounds are designated "C". The pH of 1% by wt. aqueous solutions were also measured and the results are also shown in table 1. Formulations of the toilet bar bases 1, 2, and 3 are provided in table 2. The bar bases were formulated by blending all ingredients except the latent acidifier for about 30–40 minutes at temperatures of 180–230 F. After that, the latent acidifier is added and mixed for another few minutes until a uniform mixture is obtained. It is crucial that the latent acidifier is not added when high levels of free water are present. The latent acidifier could also be added in the chip mixer after the batch has been cooled and solidified in a spray dryer or a chill roll. This is followed by extrusion and stamping into a bar.

TABLE 1

AQUEOUS SLURRY pH VALUES

| | Inventive/ Comparative | 1% Solution | Base 1 | Base 2 | Base 3 |
|---|---|---|---|---|---|
| Base (control) | — | 7.0 | 7.0 | 9.1 | 10.4 |
| Aluminium Sulfate | I | 3.1 | 3.1 | 8.2 | 9.6 |
| Ammonium Chloride | I | 4.9 | 6.5 | 8.7 | 9.1 |
| Ammonium Acetate | I | 6.9 | 6.8 | 8.9 | 9.5 |
| Ammonium Phosphate | I | 4.2 | 6.1 | 7.6 | 8.7 |
| Ammonium Sulfate | I | 5.0 | 6.7 | 8.9 | 9.4 |
| Calcium Acetate | I | 8.2 | 5.2 | 8.1 | 10.1 |
| Calcium Carbonate | C | 9.2 | 7.0 | 9.0 | 10.6 |
| Calcium Chloride | I | 9.3 | 4.2 | 6.9 | 9.8 |
| Calcium Hydroxide | C | 11.8 | 11.9 | 12.1 | 11.9 |
| Calcium Nitrate | I | 5.3 | 5.2 | 8.6 | 10.1 |
| Calcium Phosphate | I | 3.7 | 5.4 | 7.2 | 8.6 |
| Calcium Sulfate | I | 9.6 | 4.9 | 8.8 | 10.2 |
| Ferric Sulfate | I | 1.7 | 1.5 | 7.5 | 9.1 |
| Magnesium Chloride | I | 5.2 | 5.9 | 8.4 | 10.0 |
| Magnesium Sulfate | I | 6.5 | 6.2 | 8.6 | 10.2 |
| Magnesium/ Aluminium Silicate | C | 10.1 | 7.1 | 9.0 | 10.3 |
| Sodium Bicarbonate | C | 8.3 | 7.5 | 8.8 | 9.4 |
| Sodium Chloride | C | 8.1 | 6.7 | 8.7 | 10.1 |
| Sodium Phosphate | C | 9.1 | 7.2 | 8.9 | 10.2 |
| Sodium Sulfate | C | 9.1 | 6.9 | 8.9 | 10.3 |
| Silica | C | 8.2 | 7.0 | 8.9 | 9.9 |

It was found that certain salts of specific acidic metal cations such as $Fe^{3+}$, $Fe^{2+}$, $Al^{3+}$, $Cr^{2+}$, $Cu^{2+}$, and $Ni^{2+}$ including sulfates, nitrates, chlorides, phosphates and acetates gave a latent acidification effect. In addition, other salts of certain conjugate acids of weak bases such as ammonium, and other salts of other Group II cations such as calcium and magnesium also gave a latent acidification effect. Surprisingly, certain salts, such as inventive calcium sulfate that gave an alkaline effect in aqueous solution provided a latent acidification effect in one or more toilet bar formulations.

TABLE 2

Base formulations used in Example 1

| Component | Base 1 Wt. % | Base 2 Wt. % | Base 3 Wt. % |
|---|---|---|---|
| Soap (blend composition) | 10 (3 stearic, 1.3 coco, 5.7 tallow) | 55 (20 coco, 35 tallow | 82 (15 coco, 67 tallow) |
| Sodium Cocyl Isethionate | 50 | 20 | 0 |
| Fatty Acids (C10 to C18) | 23 | 7 | 0 |

TABLE 2-continued

Base formulations used in Example 1

| Component | Base 1 Wt. % | Base 2 Wt. % | Base 3 Wt. % |
|---|---|---|---|
| Cocoamidopropyl betaine | 2.8 | 0 | 0 |
| Sodium isethionate + sodium chloride | 6 | 6 | 0 |
| Total Water | 5 | About 12 | About 13 |
| Free Water | 0–2 | 9–12 | 12–13 |

EXAMPLE 2

The yield stress (hardness) and aqueous slurry pH were evaluated for several bars having formulation bases 1 and 2 formulated with various inventive latent acidifiers and comparative compounds at the 5 and 10% by wt. levels. It was found that there is a significant drop in pH with inventive latent acidifier calcium sulfate versus comparative sodium sulfate. Furthermore, although the pH drops, the hardness of the inventive bar changes very little. The results are shown in tables 3 and 4. Inventive bars 2–4 use various latent acidifiers at 10% by wt. The aqueous slurry pH decreases dramatically as compared to the Comparative formulas 1–3. The pH reduction increases with increasing concentration of the latent acidifier. In all cases, the bar hardness did not show a significant drop when comparing bars with different concentration levels of latent acidifiers.

TABLE 3

COMPARISON OF BASE 1 COMPARATIVE AND INVENTIVE BARS.

| ingredients | Base 1 (Control) | Comparative 1 | Inventive 1 |
|---|---|---|---|
| Base 1 (parts) | 10 | 9 | 9 |
| Sodium Sulfate (parts) | 0 | 1 | 0 |
| Calcium Sulfate (parts) | 0 | | 1 |
| $R_{ys}$ | — | 1.13 | 1.22 |
| Bar Hardness | ys = 164 kPa @ 99 F. | ys = 186 kPa @ 97 F. | ys = 200 kPa @ 96 F. |
| pH | 7 | 6.86 | 5.3 |

TABLE 4

FORMULATIONS OF BARS PREPARED WITH INVENTIVE LATENT ACIDIFIERS AND COMPARATIVE SALTS. pH AND HARDNESS RESULTS.

| Ingredients | Inventive 2 | Comparitive 2 | Base 2 (Control) | Inventive 3 | Inventive 4 |
|---|---|---|---|---|---|
| Base 1 | | | | 9 | 9 |
| Base 2 | 9 | 9 | 10 | | |
| Calcium Sulfate | 1.0 | | | | |
| Ammonium Sulfate | | | | | 1 |
| Aluminum Sulfate | | | | | |
| Magnesium Sulfate | | | | 1 | |
| Sodium Sulfate | | 1 | | | |
| PH of 10% Aqueous Slurry | 8.0 | 9.03 | 9.0 | 6.3 | 6.3 |

TABLE 4-continued

FORMULATIONS OF BARS PREPARED WITH INVENTIVE LATENT ACIDIFIERS AND COMPARATIVE SALTS. pH AND HARDNESS RESULTS.

| Ingredients | Inventive 2 | Comparitive 2 | Base 2 (Control) | Inventive 3 | Inventive 4 |
|---|---|---|---|---|---|
| Rys | 0.57 | 0.62 | — | 1 | 1.06 |
| Bar Hardness | 107 kPa @ 102 F. | 116 kPa @ 100 F. | 186 kPa @ 97 F. | 164 kPa @ 95 F. | 175 kPa @ 98 F. |

EXAMPLE 3

Forearm Controlled Application Test (FCAT) Results

Bar base formulation 1 with 5 and 10% by wt. of latent acidifier calcium sulfate were compared to a base 1 control formulation without calcium sulfate and bar base formulation 2 with 5 and 10% by wt. of latent acidifier calcium sulfate were compared to a base 2 control formulation without calcium sulfate in separate FCAT tests. The results are shown in tables 5 and 6 respectively, and the description of the FCAT procedure is given below.

TABLE 5

Final (Day 5) Data Summary for FCAT for Base 1 Toilet Bar*

| Bar Product | Visual Dryness | Visual Erythema | Corneometer | Skicon | Evaporimeter (TEWL) |
|---|---|---|---|---|---|
| Base 1 control | 0.74 | 0.74 | −5.35 | −63.89 | 2.80 |
| Base 1 + 5% $CaSO_4$ | 0.89 | 0.64 | −5.97 | −46.18 | 3.15 |
| Base 1 + 10% $CaSO_4$ | 0.87 | 0.57 | −5.67 | −46.87 | 2.93 |

*All values represent mean change from baseline.

TABLE 6

Final (Day 5) Data Summary for FCAT for Base 2 Toilet Bar*

| Bar Product | Visual Dryness | Visual Erythema | Corneometer | Skicon | Evaporimeter (TEWL) |
|---|---|---|---|---|---|
| Base 2 control | 1.57 | 1.29 | −11.35 | −101.34 | 5.36 |
| Base 2 + 5% $CaSO_4$ | 1.41 | 1.10 | −9.29 | −90.89 | 4.51 |
| Base 2 + 10% $CaSO_4$ | 0.93 | 0.78 | −4.08 | −60.52 | 2.73 |

Climactic conditions: For the Base 1 study the climactic conditions during the test included outside high temperatures ranging from −2.8 to 8.4 C. during the day and from −14.2 to −5.7 C. during the night. For the Base 2 study the climactic conditions during the test included outside high temperatures ranging from 1.6 to 13.5 C. during the day and from −14.2 to 2.6 C. during the night. Mean Dew Points ranged from −14.5 to −2.6 C. indicating that cold/dry conditions occurred during both tests. Snowfall was reported on one day of the Bar 1 test.

Overall impression of bar mildness

Lower values for Visual Dryness, Visual Erythema, and TEWL and higher values for Corneometer and Skicon indicate greater mildness.

Base 1+5% $CaSO_4$ and Base 1+10% $CaSO_4$ is milder than Base 1 control.

Base 2+10% $CaSO_4$ is milder than Base 2+5% $CaSO_4$ which is milder than Base 2 control.

Description of Test Methods

Method for Measuring Aqueous Slurry pH

Nine grams of the base formula and one gram of the latent acidifier (or a comparative compound) were blended together with 90 g of water to create a 10% slurry. The pH of the slurry was then measured at 25 C.

Method for Calculation of Yield Stress with Cheese Cutter Device

An approximate value for yield stress can be determined by the cheese cutter method. The principle of the measurement is that a wire penetrating into a material with a constant force will come to rest when the force on the wire due to stress balances the weight. The force balance is:

Weight driving wire=force on wire due to material stress $$mg=KysID$$

where m=mass driving wire (actual mass used in calculation is the mass placed on the device plus 56 grams, because the arm exerts that extra weight on the sample)

g=gravitational constant, 9.8 m/s2 ys=yield stress

I=length of wire penetrating soap after 1 minute

D=diameter of wire (take D=0.6 mm for our device)

K=a geometrical constant

The final equation is:

$$ys=(3/8)mg/(ID)$$

Procedure

Cut a square of soap and position on the yield stress device. Place a mass on the yield stress device while holding the arm. 400 g is an appropriate mass, although less might be needed for a very soft material. Gently lower the arm so the wire just touches the soap and let the arm go. Stop the vertical motion of the arm after one minute, and push the soap through the wire horizontally to cut a wedge out of the sample. Take the mass off the device and then measure the length of the cut in the sample. The wire would continue to cut the soap at a slow rate, but we use the length at one minute as the final value. Measure the temperature of the soap while the test proceeds.

Sample Calculation

A 400 gram weight is used on the yield stress device and a 22 mm slice is measured where the wire has cut the soap after 1 minute. Assuming the diameter of the wire is 0.6 mm, the approximate yield stress is $$\frac{(3/8)\ (400+56)\ [g]\ 9.8\ [m/sec2]\ 10-3\ [kg/g]}{22\ [mm]\ 0.6\ [mm]\ 10-6\ [m2/mm2]} = 1.3105 \text{ Pa or } 130 \text{ kPa}$$

Forearm Controlled Application Test (FCAT) Clinical Test Methodology

This controlled washing test is similar to that described by Ertel et al (A forearm controlled application technique for estimating the relative mildness of personal cleansing products, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores >1.0 and erythema scores >0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Bar Products

1. Both arms are washed simultaneously. Test sites are treated in a sequential manner starting with the site closest to the flex area, ending with the site proximal to the wrist.
2. The sites closest to the flex area of the inner forearm of both the right and left arm are moistened with warm water (90°–100° F.).
3. A moistened Masslinn towel is rubbed in a circular motion on a wetted test bar for approximately 6 seconds by studypersonnel which will result in 0.2–0.5 g of product to be dispensed.
4. The site is washed with the designated product for 10 seconds followed by a 90-second lather retention phase.
5. The above procedure (1–4) is then repeated for each of the test sites. Sites are then be rinsed for fifteen seconds and patted dry.
6. Upon completion the entire procedure is repeated (two washes/session).

For Liquid Products: A technician will prepare liquid products just prior to the wash session by dispensing between 0.1 g and 0.5 g of product either directly onto the skin or a moistened Maslinn towel or alternative application material. The washing procedure outlined above will then be used.

Evaluation Methods

Baseline visual assessments are made prior to the start of the product application phase, and immediately before each wash session to evaluate dryness and erythema thereafter. The final visual evaluation is conducted on the afternoon of the final day. Washing of a test site will be discontinued if a clinical dryness or erythema score of >4.0 is reached, or at the subject's request. If only one arm is discontinued, the remaining arm will continue to be washed according to schedule. The same evaluator under conditions that are consistent throughout the study will conduct all of the visual evaluations. The 0–6 grading scale shown in Table 7 is used to assess the test sites for dryness and erythema. To maintain the evaluator's blindness to product assignment, visual assessments are conducted in a separate area away from the product application area.

TABLE 7

Eythema and Dryness grading scale.

| Grade | Erythema | Dryness |
|---|---|---|
| 0 | None | None |
| 1.0 | Barely perceptible | Patches of slight powderiness and redness occasional patches of small scales may be seen. Distribution generalized. |
| 2.0 | Slight redness | Generalized slight powderiness. Early cracking or occasional small lifting scales may be present |
| 3.0 | Moderate redness | Generalized moderate powderiness and/or heavy cracking and lifting scales. |
| 4.0 | Heavy or substantial | Generalized heavy powderiness and/or redness heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study.

A single Servo-Med Evaporimeter (TEWL) and three Skicon measurements will be taken on each test site, at baseline (prior to start of the first wash) and at the endpoint session (three hours after the last wash on Friday, or three hours after the wash where the subject receives a termination grade of 4 or greater). Subjects must equilibrate in the instrument room for a minimum of 30 minutes, exposing their arms. Subjects with baseline TEWL measurements of >10, which may be indicative of barrier damage, are not included in the product application phase of study.

Data Analysis

Within Test Product Effects

This protocol adopts as a working assumption the view promulgated by Ertel et al (Ertel, K. D., G. H. Keswick, and P. B. Bryant. Forearm controlled application technique for estimating the relative mildness of personal cleansing products., J. Soc.Cosmet. Chem., 46, 67 (1995)) that the dryness and erythema scales are linear. Hence, parametric statistical methods will be used. The effects of each test product will be examined by comparing the clinical grade at each time point versus the baseline clinical grade using a paired t-test. Statistical significance will be determined at the 90% confidence level (p-value 0.10) to determine if treatment results are statistically different from their baseline score and in which direction. (G. W. Snedecor and W. G. Cochran, Statistical Methods. Ames, Iowa. The Iowa State University Press, 1980, pp.84–86).

Between Test Product Effects

For all treatments, differences will be statistically compared using an analysis of variance with panelist acting as a block to compare the extent of "change from baseline"

among the treatments. Following the Ertel et al published model approach, the fixed effects analysis of variance is intended to account for varying skin conditions along the volar forearm surface as well as side (left arm versus right arm) differences.

The general model is:

$$\text{response } ijklm = \mu + Ti + Sj + Ak + Pl + ljk + \xi ijklm$$

where $\mu$=the grand mean

T=effect due to treatment i

S=effect due to treatment site j

A=effect due to the side (arm), k, on which the treatment appears

P=effect due to subject 1 l=a site * side interaction term

ξ=an error term that includes error due to the various effects & experimental error, m.

with all effects other than error modeled as fixed effects.

If overall statistically significant differences are detected, pairwise treatment comparisons will be implemented by comparing the least square means using either Fisher's Least Significant Difference test (LSD) or Dunneft's test (if comparing treatments to a common control). The least square means are more accurate estimators than the regular means in that they adjust for other terms in the model and rectify slight imbalances which may sometimes occur due to missing data.

In addition, for each attribute, a survival analysis will examine treatment performance over wash sessions. The analysis will incorporate the number of wash sessions that a subject's treatment site is actually washed in the study. If the treatment site is discontinued, then the site's survival time is determined at that evaluation. An overlay plot of the estimated survival function for each treatment group will be examined. The Log-Rank test statistic will be computed to test for homogeneity of treatment groups. This test will tell if the survival functions are the same for each of the treatment groups.

2. Transepidermal Water Loss (TEWL)

The ServoMed Evaporimeter Model EP 1D, (ServoMed Inc, Broomall, Pa.) was used to quantify the rates of transepidermal water loss following the procedures similar to those outlined by Murahata et al ("The use of transepidermal water loss to measure and predict the irritation response to surfactants" Int. J. Cos. Science 8, 225 (1986)). TEWL provides a quantitative measure of the integrity of the stratum corneum barrier function and the relative effect of cleansers.

The operating principle of the instrument is based on Fick's law where $$(1/A)(dm/dt) = -D(dp/dx)$$

where

A=area of the surface (m 2)

m=weight of transported water (g)

t=time (hr)

D=constant, 0.0877 g-1h-1 (mm Hg)-1 related to the diffusion coefficient of water p=partial pressure of water vapor in air (mm Hg)

x=distance of the sensor from the skin surface (m)

The evaporation rate, dm/dt, is proportional to the partial pressure gradient, dp/dx. The evaporation rate can be determined by measuring the partial pressures at two points whose distance above the skin is different and known, and where these points are within a range of 15–20 mm above the skin surface.

The general clinical requirements are as follows:

1. All panelists are equilibrated for a minimum of fifteen minutes before measurements in a test room in which the temperature is controlled to 21+/−1° C. and 50+/−5% RH respectively.
2. The test sites are measured or marked in such a way that pre and post treatment measurements can be taken at approximately the same place on the skin.
3. The probe is applied in such a way that the sensors are perpendicular to the test site, using a minimum of pressure.

Probe Calibration is achieved with a calibration set (No. 2110) which is supplied with the instrument. The kit must be housed in a thermo-insulated box to ensure an even temperature distribution around the instrument probe and calibration flask.

The three salt solution used for calibration are LiCl, [MgNO 3]2 , and K2SO4. Pre-weighed amounts of slat at high purity are supplied with the kit instrument. The solution concentrations are such that the three solutions provide a RH of Ã11.2%, Ã54.2%, and Ã97% respectively at 21° C.

General use of the instrument is as follows:

1. For normal studies, instrument readings are taken with the selector switch set for 1–100 g/m2 h range
2. The protective cap is removed from the probe and the measuring head is placed so that the Teflon capsule is applied perpendicularly to the evaluation site ensuring that a minimum pressure is applied from the probe head. To minimize deviations of the zero point, the probe head should be held by the attached rubber-insulating stopper.
3. Subject equilibration time prior to prior to evaluation is 15 minutes in a temperature/humidity controlled room (21+/−1° C. and 50+/−5% RH respectively).
4. The probe is allowed to stabilize at the test site for a minimum of 30 seconds before data acquisition. When air drafts exist and barrier damage is high it is recommended to increase the stabilization time.
5. Data is acquired during the 15 seconds period following the stabilization time.
6. Hydration The Corneometer Skin Hygrometer (Diastron Ltd., Hampshire, England) is a device widely used in the cosmetic industry. It allows high frequency, alternating voltage electrical measurements of skin capacitance to be safely made via an electrode applied to the skin surface. The parameters measured have been found to vary with skin hydration. However, they may also vary with many other factors such as skin temperature, sweat gland activity, and the composition of any applied product. The Corneometer can only give directional changes in the water content of the upper stratum corneum under favorable circumstances but even here the quantitative interpretations may prove misleading.

A widely used alternative is the Skicon Skin conductance Meter (I.B.S. Co Ltd. Shizuoka-ken, Japan).

Panelist Requirements for either instrument are as follows:

1. Subjects should equilibrate to room conditions, which are maintained at a fixed temperature and relative humidity (21+/−1° C. and 50+/−5% RH respectively) for a minimum of 15 minutes with their arms exposed. Air currents should be minimized.
2. Physical and psychological distractions should be minimized, e.g., talking and moving around.
3. Consumption during at least 1 hour before measurement of hot beverages or of any products containing caffeine should be avoided.

4. Panelists should avoid smoking for at least 30 minutes prior to measurements.

Operating Procedure

1. The probe should be lightly applied so as to cause minimum depression of the skin surface by the outer casing. The measuring surface is spring-loaded and thus the probe must be applied with sufficient pressure that the black cylinder disappears completely inside the outer casing.
2. The probe should be held perpendicular to the skin surface.
3. The operator should avoid contacting hairs on the measure site with the probe.
4. The probe should remain in contact with the skin until the instrument's signal beeper sounds (about 1 second) and then be removed. Subsequent measurements can be made immediately provided the probe surface is known to be clean.
5. A minimum of 3 individual measurements should be taken at separate points on the test area and averaged to represent the mean hydration of the site.
6. A dry paper tissue should be used to clean the probe between readings.

4. Sensory Panel Evaluation

This evaluation protocol is used to differentiate the sensory properties of soap bars and employs a trained expert sensory panel. The methodology is a variant of that initially proposed Tragon and employs a language generation step.

The panel washes with each of up to a maximum of ten bars only once each, and will use the products up to a maximum of two per day. Each panelists washes their forearms using their normal habit for up to a maximum of 10 seconds, after which time they will rinse the product from their skin under running water. The panelists quantify various product attributes, using a line scale questionnaire, at various stages of the washing process. The key attributes evaluated include:

a) Bar feel b) Lather feel and appearance of hands during the initial lathering process c) Product/lather feel on the arm during washing d) Rinsability e) Wet skin feel after rinsing f) Dry skin feel after 2 minutes The water used was 40 PPM hardness expressed as PPM $CaCO3$.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A toilet bar, comprising:

(a) about 0 to about 30% by wt. of a fatty acid soap;

(b) about 15 to about 60% by wt. of a non-soap anionic surfactant; and (c) a latent acidifier in an effective amount to yield an aqueous slurry delta pH value of more than about 0.5.

2. The toilet bar of claim 1 which contains about 0 to about 20% by wt. of a fatty acid soap.

3. The toilet bar of claim 1 which contains about 0 to 15% by wt. of a fatty acid soap.

4. The toilet bar of claim 1 which contains about 20 to about 55%; by wt. of a non-soap anionic surfactant.

5. The toilet bar of claim 1 which contains about 25 to about 50% by wt. of a non-soap anionic surfactant.

6. The toilet bar of claim 1 which contains a latent acidifier in an effective amount to yield an aqueous slurry delta pH value of more than about 1.0.

7. The toilet bar of claim 1 wherein the latent acidifier is in the concentration range of about 0.1 to 20% by wt., preferably about 1 to about 10% by wt.

8. The toilet bar of claim 1 wherein the latent acidifier is in the concentration range of about 1 to about 10% by wt.

9. The toilet bar of claim 1 wherein the fatty acid soaps include a blend of C6 to C22 soaps.

10. The toilet bar of claim 1 wherein the fatty acid soaps includes a blend of C12 to C18 soaps.

11. The toilet bar of claim 1 wherein the non-soap anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof.

12. The toilet bar of claim 1 wherein the latent acidifier is an inorganic salt.

13. The toilet bar of claim 1 wherein the latent acidifier is selected from aluminum sulfate, aluminum chloride, ammonium chloride, ammonium phosphate, aluminum chlorohydrate, aluminum-zirconium trichlorohydrate, aluminum-zirconium trichlorohydrate glycine complex, zinc sulfate, calcium acetate, calcium chloride, calcium nitrate, calcium phosphate, calcium sulfate, ferric sulfate, magnesium chloride, and magnesium sulfate.

14. The toilet bar of claim 1 wherein the amount of free water is less than about 10% by wt.

15. The toilet bar of claim 1 wherein the amount of free water is less than about 7% by wt.

16. The toilet bar of claim 1 wherein the amount of free water is less than about 3% by wt.

17. The toilet bar of claim 1 further comprising a $R_{ys}$ value in the range of about 0.70 to about 1.3.

18. The toilet bar of claim 17 wherein the $R_{ys}$ value is in the range of about 0.8 to about 1.2.

19. The toilet bar of claim 1 wherein there is at least 0.1% by wt. of a fatty acid soap.

20. A toilet bar, comprising:

(a) about 30 to about 80% by wt. of a fatty acid soap;

(b) about 5 to about 40% by wt. of a non-soap anionic surfactant; and (c) a latent acidifier in an effective amount to yield an aqueous slurry delta pH value of more than about 0.5.

21. The toilet bar of claim 20 which contains about 40 to about 70% by wt. of a fatty acid soap.

22. The toilet bar of claim 20 which contains about 50% to about 60% by wt. of a fatty acid soap.

23. The toilet bar of claim 20 which contains about 7 to about 30% by wt. of a non-soap anionic surfactant.

24. The toilet bar of claim 20 which contains about 10 to about 20% by wt. of a non-soap anionic surfactant.

25. The toilet bar of claim 20 which contains a latent acidifier in an effective amount to yield an aqueous slurry delta pH value of more than about 1.0.

26. The toilet bar of claim 20 wherein the latent acidifier is in the concentration range of about 0.1 to about 20% by wt.

27. The toilet bar of claim 20 wherein the latent acidifier is in the concentration range of about 1 to about 10% by wt.

28. The toilet bar of claim 20 wherein the fatty acid soaps include a blend of C6 to C22 soaps.

29. The toilet bar of claim 20 wherein the fatty acid soaps include a blend of C12 to C18 soaps.

30. The toilet bar of claim 20 wherein the non-soap anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof.

31. The toilet bar of claim 20 wherein the latent acidifier is an inorganic salt.

32. The toilet bar of claim 20 wherein the latent acidifier is selected from aluminum sulfate, aluminum chloride, ammonium chloride, ammonium phosphate, aluminum chlorohydrate, aluminum-zirconium trichlorohydrate, aluminum-zirconium trichlorohydrate glycine complex, zinc sulfate, calcium acetate, calcium chloride, calcium nitrate, calcium phosphate, calcium sulfate, ferric sulfate, magnesium chloride, and magnesium sulfate.

33. The toilet bar of claim 20 wherein the amount of free water is less than about 25% by wt.

34. The toilet bar of claim 20 wherein the amount of free water is less than about 20% by wt.

35. The toilet bar of claim 20 wherein the amount of free water is less than about 15% by wt.

36. The toilet bar of claim 20 further comorising a $R_{ys}$ value in the range of about 0.70 to about 1.3.

37. The toilet bar of claim 36 wherein the $R_{ys}$ value is in the range of about 0.8 to about 1.2.

38. A toilet bar, comprising:

(a) about 40 to about 85% by wt. of a fatty acid soap;

(b) about 0 to about 10% by wt. of a non-soap anionic surfactant; and (c) a latent acidifier in an effective amount to yield an aqueous slurry delta pH value of more than about 0.5.

39. The toilet bar of claim 38 which contains about 50 to about 80% by wt. of a fatty acid soap.

40. The toilet bar of claim 38 which contains about 60 to about 75% by wt. of a fatty acid soap.

41. The toilet bar of claim 38 which contains about 0 to about 7% by wt. of a non-soap anionic surfactant.

42. The toilet bar of claim 38 which contains about 0 to about 5% by wt. of a non-soap anionic surfactant.

43. The toilet bar of claim 38 which contains a latent acidifier in an effective amount to yield an aqueous slurry delta pH value of more than about 1.0.

44. The toilet bar of claim 38 wherein the latent acidifier is in the concentration range of about 0.1 to about 20% by wt.

45. The toilet bar of claim 38 wherein the latent acidifier is in the concentration range of about 1 to about 10% by wt.

46. The toilet bar of claim 38 wherein the fatty acid soaps include a blend of C6 to C22 soaps.

47. The toilet bar of claim 38 wherein the fatty acid soaps include a blend of C12 to C18 soaps.

48. The toilet bar of claim 38 wherein the non-soap anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof.

49. The toilet bar of claim 38 wherein the latent acidifier is an inorganic salt.

50. The toilet bar of claim 38 wherein the latent acidifier is selected from aluminum sulfate, aluminum chloride, ammonium chloride, ammonium phosphate, aluminum chlorohydrate, aluminum-zirconium trichlorohydrate, aluminum-zirconium trichlorohydrate glycine complex, zinc sulfate, calcium acetate, calcium chloride, calcium nitrate, calcium phosphate, calcium sulfate, ferric sulfate, magnesium chloride, and magnesium sulfate.

51. The toilet bar of claim 38 wherein the amount of free water is in the range of about 5 to about 30% by wt.

52. The toilet bar of claim 38 wherein the amount of free water is in the range of about 7 to about 25% by wt.

53. The toilet bar of claim 38 wherein the amount of free water is in the range of about 10 to about 20% by wt.

54. The toilet bar of claim 38 further comprising a $R_{ys}$ value in the range of about 0.70 to about 1.3.

55. The toilet bar of claim 54 wherein the $R_{ys}$ value is in the range of about 0.8 to about 1.2.

56. The toilet bar of claim 38 wherein there is at least 0.1% by wt. of a non-soap anionic detergent.

* * * * *